(12) United States Patent
Chiou et al.

(10) Patent No.: US 9,746,437 B1
(45) Date of Patent: Aug. 29, 2017

(54) CMOS-BASED PROCESS FOR MANUFACTURING A SEMICONDUCTOR GAS SENSOR

(71) Applicant: NATIONAL CHIAO TUNG UNIVERSITY, Hsinchu (TW)

(72) Inventors: Jin-Chern Chiou, Hsinchu (TW); Shang-Wei Tsai, Jinhu Township, Kinmen County (TW)

(73) Assignee: NATIONAL CHIAO TUNG UNIVERSITY (TW)

( * ) Notice: Subject to any disclaimer, the term of this patent is extended or adjusted under 35 U.S.C. 154(b) by 0 days.

(21) Appl. No.: 15/398,025

(22) Filed: Jan. 4, 2017

(30) Foreign Application Priority Data

Aug. 3, 2016 (TW) .............................. 105124541 A

(51) Int. Cl.

| H01L 21/00 | (2006.01) |
|---|---|
| G01N 27/12 | (2006.01) |
| H01L 29/08 | (2006.01) |
| H01L 21/8234 | (2006.01) |
| H01L 29/49 | (2006.01) |
| H01L 21/28 | (2006.01) |
| H01L 21/311 | (2006.01) |

(52) U.S. Cl.
CPC ..... *G01N 27/128* (2013.01); *H01L 21/28035* (2013.01); *H01L 21/31116* (2013.01); *H01L 21/823437* (2013.01); *H01L 21/823475* (2013.01); *H01L 29/0847* (2013.01); *H01L 29/4916* (2013.01)

(58) Field of Classification Search
CPC ............. H01L 29/0847; H01L 29/4916; H01L 21/823475; H01L 21/823437; H01L 21/28035; H01L 21/31116
See application file for complete search history.

(56) References Cited

U.S. PATENT DOCUMENTS

| 7,157,054 B2 | 1/2007 | Toyoda et al. |
| 7,495,300 B2 | 2/2009 | Gardner et al. |
| 2009/0126460 A1 | 5/2009 | Gardner et al. |
| 2014/0102172 A1* | 4/2014 | Daamen ............... G01N 27/223 73/25.03 |
| 2016/0266061 A1* | 9/2016 | Yu ....................... G01L 19/0092 |

OTHER PUBLICATIONS

Syed Z. Ali et al., "Tungsten-Based SOI Microhotplates for Smart Gas Sensors," Journal of Microelectromechanical Systems, vol. 17, No. 6, pp. 1408-1417, Dec. 2008.
Chih-Cheng Lu et al. "Multi-field Simulations and Characterization of CMOS-MEMS High-Temperature Smart Gas Sensors Based on SOI Technology," IOP Publishing Ltd., Journal of Micromechanics and Microengineering, 18 (2008) 075010 (11pp).
Ming-Zhi Yang et al., "Fabrication of an Ammonia Microsensor Based on Zinc Oxide," IEEE NEMS2013, Suzhou, China, Apr. 7-10, 2013, pp. 270-273.

* cited by examiner

*Primary Examiner* — Richard Booth
(74) *Attorney, Agent, or Firm* — Brooks Kushman P.C.

(57) ABSTRACT

A CMOS-based process for manufacturing a semiconductor gas sensor includes the steps of: I) providing a semi-product, II) etching a substrate to remove a portion of the substrate and a portion of a first insulation layer so as to form a gas-sensing cavity, thereby to expose at least one sensing electrode; and III) depositing a gas-sensitive layer to cover the at least one sensing electrode.

6 Claims, 6 Drawing Sheets

CMOS-BASED PROCESS FOR MANUFACTURING A SEMICONDUCTOR GAS SENSOR

CROSS-REFERENCE TO RELATED APPLICATIONS

This application claims priority of Taiwanese Application No. 105124541, filed on Aug. 3, 2016.

TECHNICAL FIELD

The disclosure relates to a CMOS-based process for manufacturing a semiconductor gas sensor, and more particularly to a CMOS-based process for manufacturing a semiconductor gas sensor in which a micro-heater and a sensing electrode are formed directly in a standard CMOS-MEMS process. The disclosure also relates to a semiconductor gas sensor manufactured by the CMOS-based process.

BACKGROUND

With rapidly increasing development of IOT (internet of things), it is desirable to provide a gas sensor which is capable of being combined with a portable/wearable device. In order to be integrable with the portable/wearable device, it is important to develop a gas sensor which is miniaturized, which is of low power consumption, and which is module-packaged. Generally speaking, miniaturization of the gas sensor may be achieved via a standard CMOS-MEMS (complementary metal-oxide-silicon and microelectromechanical system) process.

Referring to FIG. 1, a conventional gas sensor includes a substrate 10, an electronic circuit unit 11, and a heating-and-sensing unit 12. The electronic circuit unit 11 is primarily constituted of a drive circuit, a signal-reading circuit, and a temperature-controlling circuit, and is used for controlling the temperature of the heating-and-sensing unit 12 and for reading the signal from the heating-and-sensing unit 12. The heating-and-sensing unit 12 includes a micro-heater 121 disposed above the substrate 10, a plurality of sensing electrodes 122 disposed above the micro-heater 121, and a gas-sensitive layer 123 covering the sensing electrodes 122. The substrate 10 is formed with a cavity 100 located below the micro-heater 121 for dissipating the heat produced by the micro-heater 121. The configurations of the micro-heater 121, the sensing electrodes 122, and the gas-sensitive layer 123 may be designed according to the material characteristics therefor via the standard CMOS-MEMS process.

Polycrystalline silicon is usually used for making the micro-heater 121 so as to withstand a high temperature at which the micro-heater 121 is operated. The sensing electrodes 122 are made from gold or platinum. However, since the sensing electrodes 122 are made in an additional step performed after the CMOS-MEMS process, the overall process for manufacturing the conventional gas sensor is relatively complicated. In addition, since the material (i.e., gold or platinum) for forming the sensing electrodes 122 is expensive, the cost for manufacturing the conventional gas sensor is relatively high.

U.S. Pat. No. 7,495,300 B2 discloses a gas-sensing semiconductor device having a configuration similar to that of the conventional gas sensor shown in FIG. 1. As described in the abstract of U.S. Pat. No. 7,495,300 B2, the gas-sensing semiconductor device is fabricated on a silicon substrate and includes at least one sensing area provided with a gas-sensing layer separated from a heater by an insulating layer. As one of the final fabrication steps, the substrate is back-etched so as to form a thin membrane in the sensing area. The back-etch and the gas-sensing layer formation are carried out post-CMOS.

Referring to FIG. 2, another conventional gas sensor is illustrated in which the sensing electrodes 122 of the heating-and-sensing unit 12 may be made from the polycrystalline silicon via the standard CMOS-MEMS process. However, the sensing electrodes 122 should be arranged at two opposite sides of the micro-heater 121. As a result, the gas sensor manufactured thereby has a relatively large size, and the heat radiated by the micro-heater 121 may not be efficiently conducted to the sensing electrodes 122.

Therefore, it is desirable in the art to develop a gas sensor which may overcome the aforesaid disadvantages of the conventional gas sensors.

SUMMARY

An object of the disclosure is to provide a process for manufacturing a semiconductor gas sensor in which a micro-heater and a sensing electrode may be formed directly in a standard CMOS-MEMS process.

According to a first aspect of the disclosure, there is provided a CMOS-based process for making a semi-product for manufacturing a semiconductor gas sensor, comprising the steps of:

a) preparing a substrate made from a semiconductor material and having a first surface and a second surface opposite to the first surface;

b) depositing a first insulation layer on the first surface of the substrate;

c) forming in an integrated circuit area an N-type doped region and a P-type doped region under the first surface of the substrate;

d) simultaneously forming on the first insulation layer a plurality of gate electrodes and at least one sensing electrode using a depositable conductive material, each of the gate electrodes being located above a corresponding one of the N-type and P-type doped regions, the at least one sensing electrode being located in a sensing area;

e) depositing a second insulation layer on the first insulation layer so as to cover the gate electrodes and the at least one sensing electrode;

f) forming a P-type doped source sub-region and a P-type doped drain sub-region in the N-type doped region and an N-type doped source sub-region and an N-type doped drain sub-region in the P-type doped region;

g) forming a plurality of via holes each of which extends through the first and second insulation layers and communicates with a corresponding one of the P-type doped source sub-region, the P-type doped drain sub-region, the N-type doped source sub-region, and the N-type doped drain sub-region;

h) simultaneously forming on the second insulation layer a micro-heater and a plurality of connecting ends of connecting portions using a resistive heating material, the micro-heater being in the sensing area and above the at least one sensing electrode, each of the connecting portions extending to fill a corresponding one of the via holes; and i) depositing a third insulation layer on the second insulation layer to cover the micro-heater while leaving the connecting ends of the connecting portions exposed.

According to a second aspect of the disclosure, there is provided a CMOS-based process for manufacturing a semiconductor gas sensor, comprising the steps of:

I) providing a semi-product made by the method described above;

II) etching from the second surface of the substrate to remove a portion of the substrate and a portion of the first insulation layer so as to form a gas-sensing cavity, thereby to expose the at least one sensing electrode; and III) depositing a gas-sensitive layer to cover the at least one sensing electrode.

According to a third aspect of the disclosure, there is provided a semiconductor gas sensor manufactured by the CMOS-based process described above.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
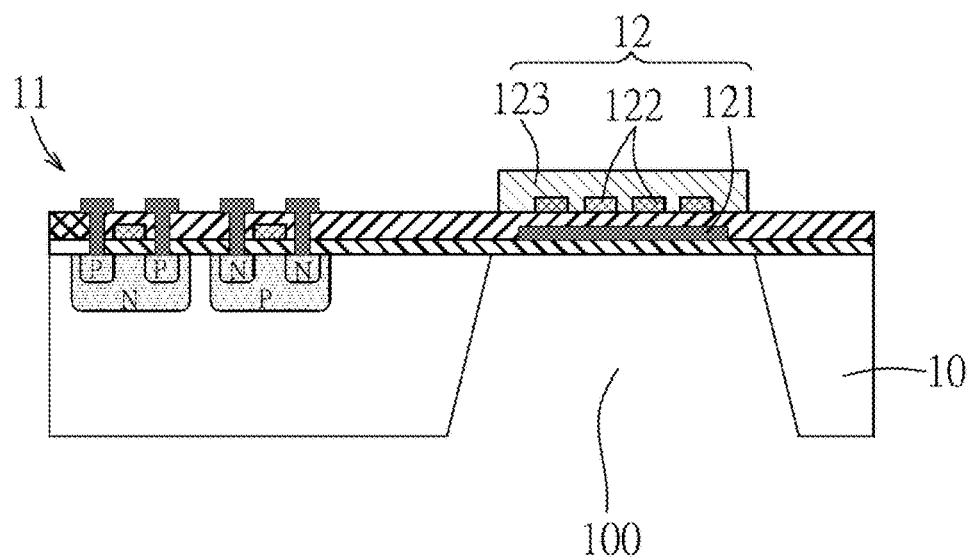
FIG. 1 is a schematic sectional view illustrating a conventional gas sensor.
Figure 2:
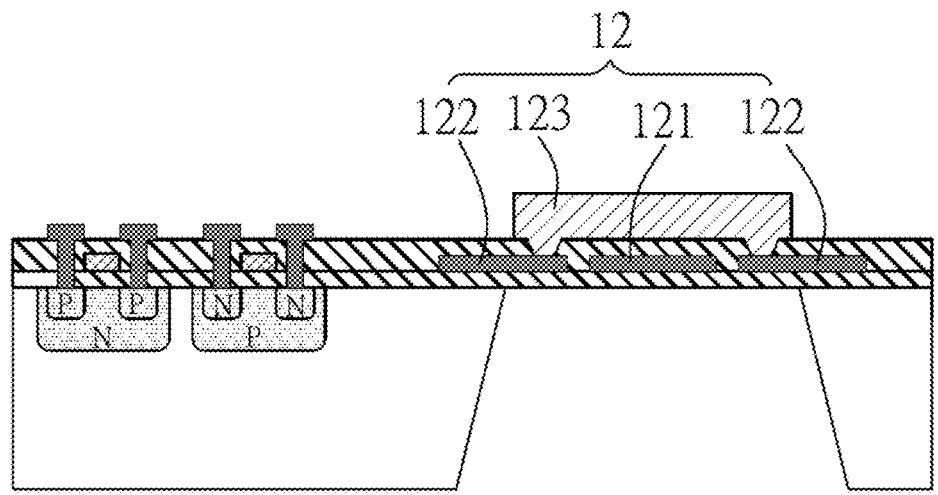
FIG. 2 is a schematic sectional view illustrating another conventional gas sensor.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 3:
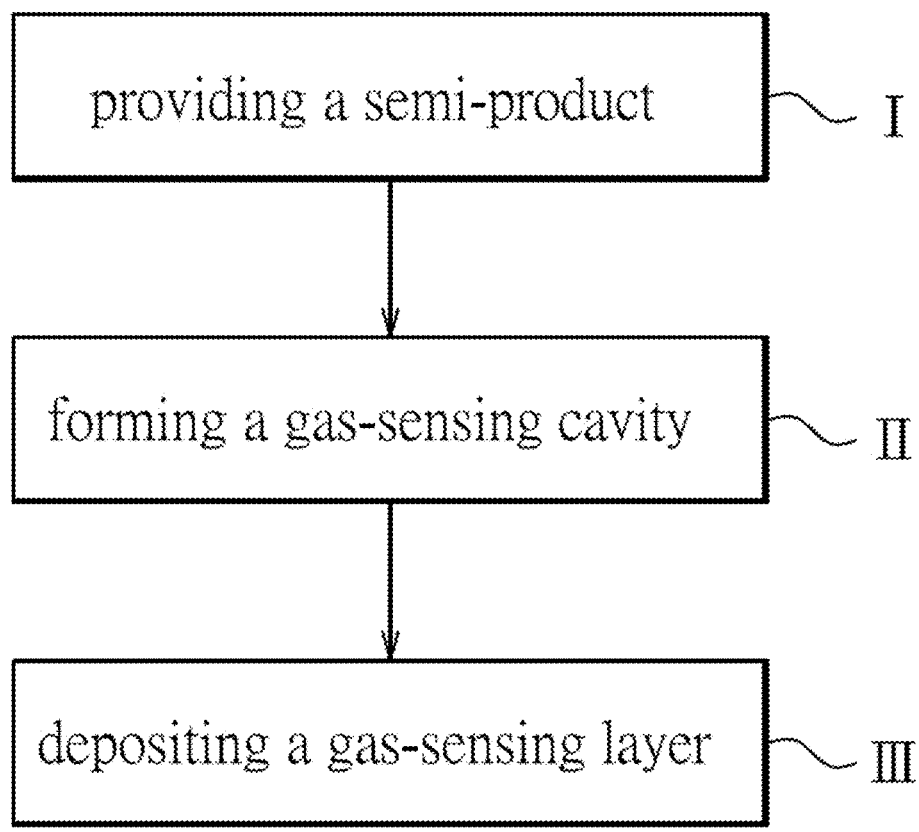
FIG. 3 is a flow diagram of an embodiment of a CMOS-based process for manufacturing a semiconductor gas sensor according to the disclosure.

Referring to FIG. 3, the embodiment of a CMOS-based process for manufacturing a semiconductor gas sensor according to the disclosure includes the steps of: I) providing a semi-product; II) form a gas-sensing cavity; and III) depositing a gas-sensitive layer. Specifically, the CMOS-based process is a standard CMOS-MEMS process (a complementary metal-oxide-silicon and microelectromechanical system process).

Referring to FIGS. 4-10, the semi-product provided in step I) is made by a CMOS-based process which includes following steps a), b), c), d), e), f), g), h), and i).

Figure 4:
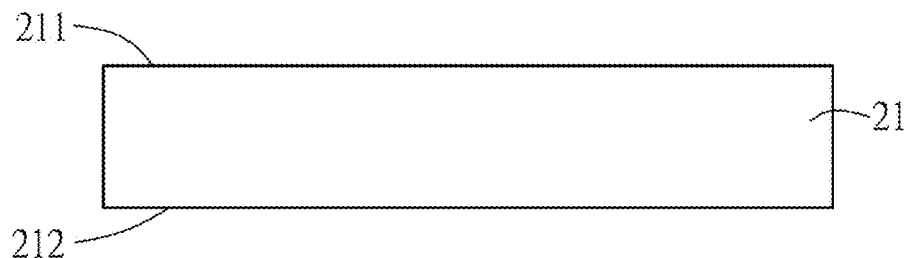
FIGS. 4-13 are schematic sectional views showing consecutive steps of the embodiment.

Referring to FIG. 4, in step a), a substrate 21 is prepared, which is made from a semiconductor material and which has a first surface 211 and a second surface 212 opposite to the first surface 211. In the embodiment, the substrate 21 illustrated is a silicon substrate.

Figure 5:
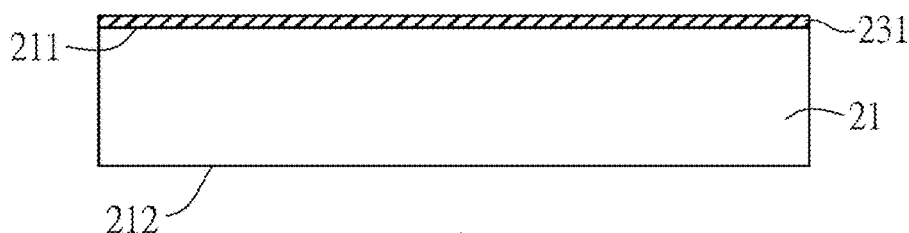

Referring to FIG. 5, in step b), a first insulation layer 231 is deposited on the first surface 211 of the substrate 21.

Figure 6:
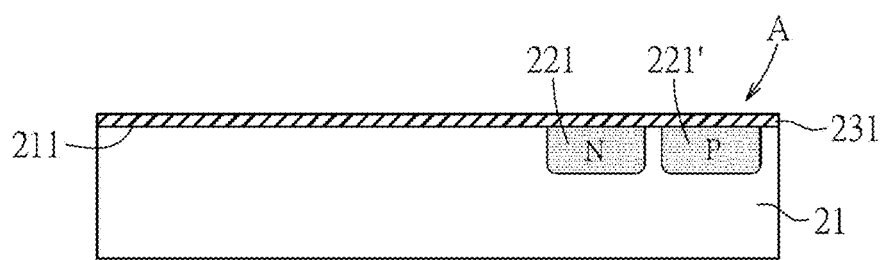

Referring to FIG. 6, in step c), in an integrated circuit area (A), an N-type doped region 221 and a P-type doped region 221' is formed under the first surface 211 of the substrate 21 by an ion diffusion procedure usually used for making a CMOS transistor in a standard IC process. One N-type doped region 221 and one P-type doped region 221' are illustrated in the embodiment. However, the number of the N-type doped region 221 and the number of the P-type doped region 221' are not to be limited.

Figure 7:
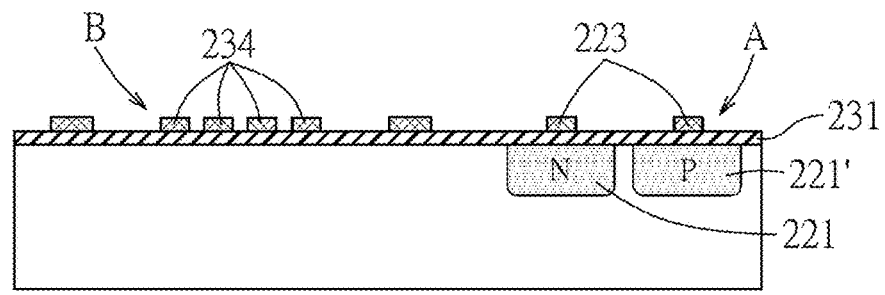

Referring to FIG. 7, in step d), a plurality of gate electrodes 223 and a plurality of sensing electrode 234 are simultaneously forming on the first insulation layer 231 using a depositable conductive material by a masking technology usually used in the standard CMOS-MEMS process. The depositable conductive material used in the embodiment is polycrystalline silicon. Two gate electrodes 223 are illustrated in the embodiment and each of the gate electrodes 223 is located above a corresponding one of the N-type and P-type doped regions 221, 221'. The sensing electrodes 234 are located in a sensing area (B).

Figure 8:
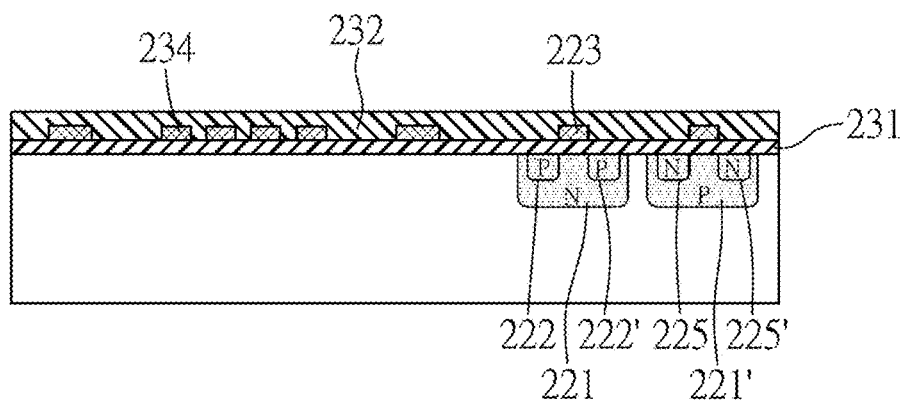

Referring to FIG. 8, in step e), a second insulation layer 232 is deposited on the first insulation layer 231 so as to cover the gate electrodes 223 and the sensing electrodes 234.

In step f), a P-type doped source sub-region 222 and a P-type doped drain sub-region 222' is formed in the N-type doped region 221 and an N-type doped source sub-region 225 and an N-type doped drain sub-region 225' is formed in the P-type doped region 221' by the ion diffusion procedure.

Figure 9:
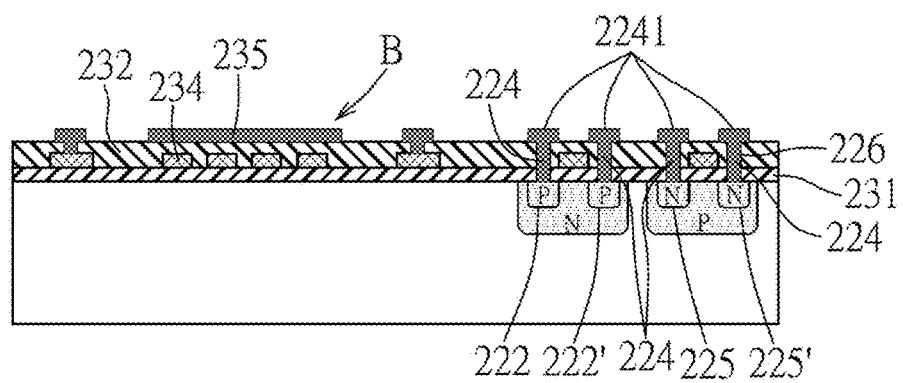

Referring to FIG. 9, in step g), a plurality of via holes 226 are formed by a lithography and etching process. Each of the via holes 226 extends through the first and second insulation layers 231, 232 and communicates with a corresponding one of the P-type doped source sub-region 222, the P-type doped drain sub-region 222', the N-type doped source sub-region 225, and the N-type doped drain sub-region 225'.

In step h), a micro-heater 235 and a plurality of connecting ends 2241 of connecting portions 224 are simultaneously formed on the second insulation layer 232 using a resistive heating material by the masking technology. The resistive heating material suitably used in the disclosure is selected from the group consisting of tantalum nitride, tungsten, and a combination thereof. The micro-heater 235 is in the sensing area (B) and above the sensing electrodes 234, and may be configured in a meandering shape. Each of the connecting portions 224 formed from resistive heating material extends to fill a corresponding one of the via holes 226.

Figure 10:
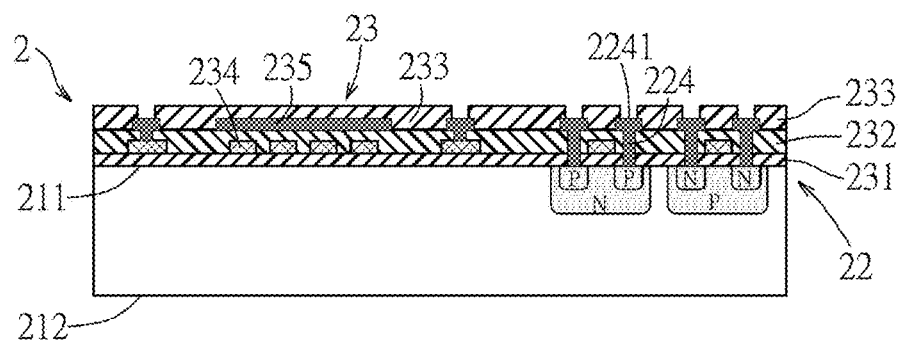

Referring to FIG. 10, in step i), a third insulation layer 233 is deposited on the second insulation layer 232 to cover the micro-heater 235 while leaving the connecting ends 2241 of the connecting portions 224 exposed so as to make the semi-product.

Figure 11:
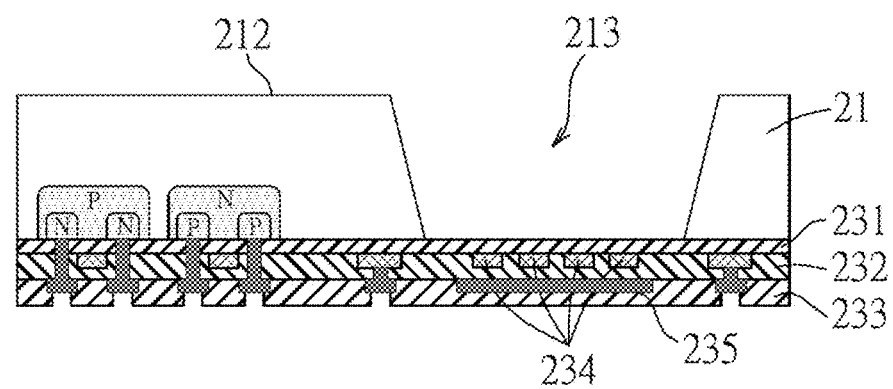
Figure 12:
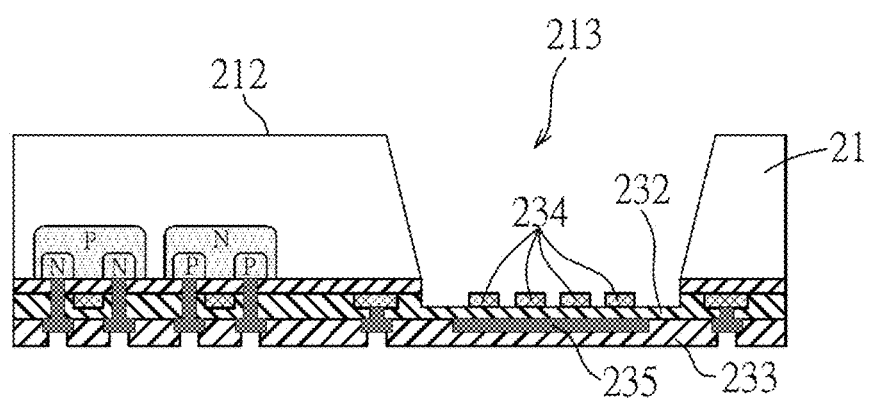

Referring to FIGS. 11 and 12, in step II), the semi-product is processed by etching from the second surface 212 of the substrate 21 to remove a portion of the substrate 21 and a portion of the first insulation layer 231 so as to form a gas-sensing cavity 213, thereby to expose the sensing electrodes 234. The gas-sensing cavity 213 may be formed by a wet etching method or a dry etching method, such as a DRIE (deep reactive ion etching) method or an ICP (inductively coupled plasma) etching method.

Figure 13:
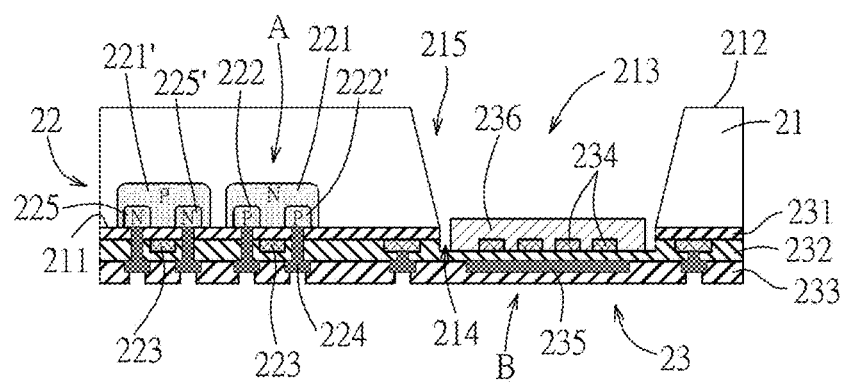

Referring to FIG. 13, in step III), a gas-sensitive layer 236 is deposited to cover the sensing electrodes 234 so as to manufacture the semiconductor gas sensor.

As shown in FIG. 13, the semiconductor gas sensor manufactured by the embodiment of the CMOS-based process according to the disclosure includes the substrate 21, the first insulation layer 231, the second insulation layer 232, the third insulation layer 233, a heating-and-sensing unit 23, and an electronic circuit unit 22.

The substrate 21 has the first surface 211 and the second surface 212 opposite to the first surface 211 and defines the gas-sensing cavity 213 which extends from the first surface 211 to the second surface 212 and which has a first opening 214 at the first surface and a second opening 125 at the second surface 212.

The first insulation layer 231 is deposited on the first surface 211 of the substrate.

The second insulation layer 232 is deposited on the first insulation layer 231.

The third insulation layer 233 is deposited on the second insulation layer 232.

The heating-and-sensing unit 23 is located in the sensing area (B) and includes the micro-heater 235, the sensing electrodes 234, and the gas-sensitive layer 236. The micro-heater 235 is formed on the second insulation layer 232 and is covered by the third insulation layer 233. The sensing electrodes 234 are formed on the second insulation layer 232, opposite to the micro-heater 235, and within the gas-sensing cavity 213 of the substrate. The gas-sensitive layer 236 covers the sensing electrodes 234 and is within the gas-sensing cavity 213 of the substrate 21.

The electronic circuit unit 22 is located in the integrated circuit area (A) and is used for driving, controlling and transducing functions. The electronic circuit unit 22 includes the N-type doped region 221, the P-type doped region 221', the gate electrodes 223, the P-type doped source sub-region 222 and the P-type doped drain sub-region 222' in the N-type doped region 221, and the N-type doped source sub-region 225 and the N-type doped drain sub-region 225' in the P-type doped region 221'.

As described above, the gate electrodes 223 and the sensing electrodes 234 may be simultaneously formed using the depositable conductive material, and the micro-heater 235 and the connecting portions 224 may be simultaneously formed using the resistive heating material in the CMOS-based process according to the disclosure. Therefore, the components including the sensing electrodes 234 and the micro-heater 235 in the semiconductor gas sensor may be formed in the CMOS-based process according to the disclosure without any additional post-CMOS-MEMES processing step.

Furthermore, since the sensing electrodes 234 and the micro-heater 235 covering the sensing electrodes 234 are formed within the gas-sensing cavity 213 of the substrate, the size of the semiconductor gas sensor manufactured by the CMOS-based process according to the disclosure may be desirably minimized.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A CMOS-based process for making a semi-product for manufacturing a semiconductor gas sensor, comprising the steps of:
   (a) preparing a substrate made from a semiconductor material and having a first surface and a second surface opposite to the first surface;
   (b) depositing a first insulation layer on the first surface of the substrate;
   (c) forming in an integrated circuit area an N-type doped region and a P-type doped region under the first surface of the substrate;
   (d) simultaneously forming on the first insulation layer a plurality of gate electrodes and at least one sensing electrode using a depositable conductive material, each of the gate electrodes being located above a corresponding one of the N-type and P-type doped regions, the at least one sensing electrode being located in a sensing area;
   (e) depositing a second insulation layer on the first insulation layer so as to cover the gate electrodes and the at least one sensing electrode;
   (f) forming a P-type doped source sub-region and a P-type doped drain sub-region in the N-type doped region and an N-type doped source sub-region and an N-type doped drain sub-region in the P-type doped region;
   (g) forming a plurality of via holes each of which extends through the first and second insulation layers and communicates with a corresponding one of the P-type doped source sub-region, the P-type doped drain sub-region, the N-type doped source sub-region, and the N-type doped drain sub-region;
   (h) simultaneously forming on the second insulation layer a micro-heater and a plurality of connecting ends of connecting portions using a resistive heating material, the micro-heater being in the sensing area and above the at least one sensing electrode, each of the connecting portions extending to fill a corresponding one of the via holes; and
   (i) depositing a third insulation layer on the second insulation layer to cover the micro-heater while leaving the connecting ends of the connecting portions exposed.

2. The method according to claim 1, wherein the depositable conductive material is polycrystalline silicon.

3. The method according to claim 1, wherein the resistive heating material is selected from the group consisting of tantalum nitride, tungsten, and a combination thereof.

4. A CMOS-based process for manufacturing a semiconductor gas sensor, comprising the steps of:
   (I) providing a semi-product made by the method according to claim 1;
   (II) etching from the second surface of the substrate to remove a portion of the substrate and a portion of the first insulation layer so as to form a gas-sensing cavity, thereby to expose the at least one sensing electrode; and (III) depositing a gas-sensitive layer to cover the at least one sensing electrode.

5. The method according to claim 4, wherein in step (II), the first insulation layer is etched via deep reactive ion etching or inductively coupled plasma etching.

6. A semiconductor gas sensor manufactured by the method according to claim 4.

* * * * *